(12) United States Patent
Chennupati et al.

(10) Patent No.: US 10,775,327 B2
(45) Date of Patent: Sep. 15, 2020

(54) EXHAUST GAS-SENSOR

(71) Applicant: TEXAS INSTRUMENTS INCORPORATED, Dallas, TX (US)

(72) Inventors: Siva RaghuRam Prasad Chennupati, Unterschleissheim (DE); Sandeep Tallada, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 168 days.

(21) Appl. No.: 15/883,162

(22) Filed: Jan. 30, 2018

(65) Prior Publication Data

US 2018/0348152 A1 Dec. 6, 2018

Related U.S. Application Data

(60) Provisional application No. 62/514,644, filed on Jun. 2, 2017.

(51) Int. Cl.
| | | |
|---|---|---|
| *G01N 24/00* | (2006.01) | |
| *G01M 15/10* | (2006.01) | |
| *F01N 11/00* | (2006.01) | |
| *F01N 3/10* | (2006.01) | |
| *B01D 46/00* | (2006.01) | |
| *G01N 33/00* | (2006.01) | |

(52) U.S. Cl.
CPC .............. *G01N 24/008* (2013.01); *F01N 3/10* (2013.01); *F01N 11/00* (2013.01); *F01N 11/007* (2013.01); *G01M 15/10* (2013.01); *G01M 15/102* (2013.01); *G01M 15/104* (2013.01); *B01D 46/0086* (2013.01); *B01D 2279/30* (2013.01); *F01N 2550/02* (2013.01); *F01N 2550/04* (2013.01); *F01N 2560/12* (2013.01); *F01N 2900/0416* (2013.01); *F01N 2900/1402* (2013.01); *F01N 2900/1606* (2013.01); *G01N 33/0036* (2013.01)

(58) Field of Classification Search
CPC .... G01N 24/008; G01N 33/0036; F01N 3/10; F01N 2900/0416; F01N 2550/04; F01N 2900/1606; F01N 2560/12; G01M 15/104; B01D 2279/30; B01D 46/0086
See application file for complete search history.

(56) References Cited

U.S. PATENT DOCUMENTS

| | | | |
|---|---|---|---|
| 8,470,070 B2 * | 6/2013 | Kulkarni | F01N 3/0232 |
| | | | 422/169 |
| 2007/0089513 A1 * | 4/2007 | Rosenau | G01D 5/24 |
| | | | 73/514.32 |
| 2010/0101409 A1 * | 4/2010 | Bromberg | F01N 3/025 |
| | | | 95/8 |

(Continued)

*Primary Examiner* — Daniel S Larkin
*Assistant Examiner* — Anthony W Megna Fuentes
(74) *Attorney, Agent, or Firm* — John R. Pessetto; Charles A. Brill; Frank D. Cimino

(57) ABSTRACT

An exhaust gas sensing system includes a channel for flow of exhaust gas, a first directional antenna, a second directional antenna, a first transmitter, a first receiver, and signal processing circuitry. The first directional antenna and the second directional antenna are disposed in the channel. The first transmitter is coupled to the first directional antenna. The first receiver is coupled to the second directional antenna. The signal processing circuitry is coupled to the first transmitter and the first receiver.

20 Claims, 3 Drawing Sheets

(56) References Cited

U.S. PATENT DOCUMENTS

| | | | |
|---|---|---|---|
| 2010/0102828 A1* | 4/2010 | Bromberg | B01D 46/0086 324/639 |
| 2013/0147493 A1* | 6/2013 | Marchetti | G01N 33/0036 324/639 |
| 2015/0358091 A1* | 12/2015 | Sappok | H04B 17/00 455/67.11 |

* cited by examiner

EXHAUST GAS-SENSOR

CROSS-REFERENCE TO RELATED APPLICATIONS

The present application claims priority to U.S. Provisional Patent Application No. 62/514,644, filed Jun. 2, 2017, titled "RF-Exhaust-Multiple-Gas Sensor," which is hereby incorporated herein by reference in its entirety.

BACKGROUND

Internal combustion engines include engine control systems that use information collected from an engine's exhaust to monitor and control the operation of the engine. For example, oxygen sensors are included in the exhaust systems of internal combustion engines and provide information regarding the ratio of air to fuel being supplied to the engine. In general, internal combustion engines need a specific air-to-fuel ratio (or ratio range) to operate correctly. When the ratio is less than desired, not all fuel in the air-fuel mixture is burned or combusted. This situation is referred to as a rich mixture or rich condition and has a negative impact on exhaust emissions. When the air-fuel ratio is higher than desired, excess oxygen is present in the air-fuel mixture. This situation is referred to as a lean mixture or lean condition. When an engine burns lean, engine performance may decrease and, in some cases, may cause engine damage and have a negative impact on exhaust emissions.

Internal combustion engines may also produce particulate emissions. For example, the exhaust produced by a diesel engine may include a significant amount of carbon particulate (soot). The exhaust system may include soot sensors that measure the amount of soot being output, so that the engine control can reduce the emission values, or apply maintenance operations to devices that remove the soot from the exhaust.

SUMMARY

Apparatus for measuring substances present in the exhaust of an internal combustion engine is disclosed herein. In one example, an exhaust gas sensing system includes a channel for flow of exhaust gas, a first directional antenna, a second directional antenna, a first transmitter, a first receiver, and signal processing circuitry. The first directional antenna and the second directional antenna are disposed in the channel. The first transmitter is coupled to the first directional antenna. The first receiver is coupled to the second directional antenna. The signal processing circuitry is coupled to the first transmitter and the first receiver.

In another example, an internal combustion engine control system includes an exhaust filter and a sensing system. The exhaust filter is coupled to an internal combustion engine. The exhaust filter includes an input port, an output port, and a filter element disposed between the input port and the output port. The sensing system includes a first directional antenna, a second directional antenna, and signal processing circuitry. The first directional antenna is disposed on an input port side of the exhaust filter. The second directional antenna is disposed on an output port side of the exhaust filter. The signal processing circuitry is coupled to the first directional antenna and the second directional antenna. The signal processing circuitry is configured to measure a plurality of substances in exhaust passing through the exhaust filter based on radio frequency signals transmitted from the first directional antenna to the second directional antenna.

In a further example, an exhaust gas sensing system includes a channel for flow of exhaust gas, a first coplanar antenna, a second coplanar antenna; a first transmitter, a first receiver, a second transmitter, a second receiver, and signal processing circuitry. The first coplanar antenna and the second coplanar antenna are disposed in the channel. The first transmitter and the second receiver are coupled to the first coplanar antenna. The first receiver and the second transmitter are coupled to the second coplanar antenna. The signal processing circuitry is coupled to the first transmitter, the first receiver, the second transmitter, and the second receiver. The signal processing circuitry is configured to measure a quantity of soot and a quantity of oxygen, and/or a quantity of any other gas of interest, in exhaust gas flowing in the channel, and to measure the quantity of oxygen based on a harmonic resonance or attenuation frequency of the oxygen or any other gases of interest.

BRIEF DESCRIPTION OF THE DRAWINGS

For a detailed description of various examples, reference will now be made to the accompanying drawings in which.

DETAILED DESCRIPTION

Figure 1:
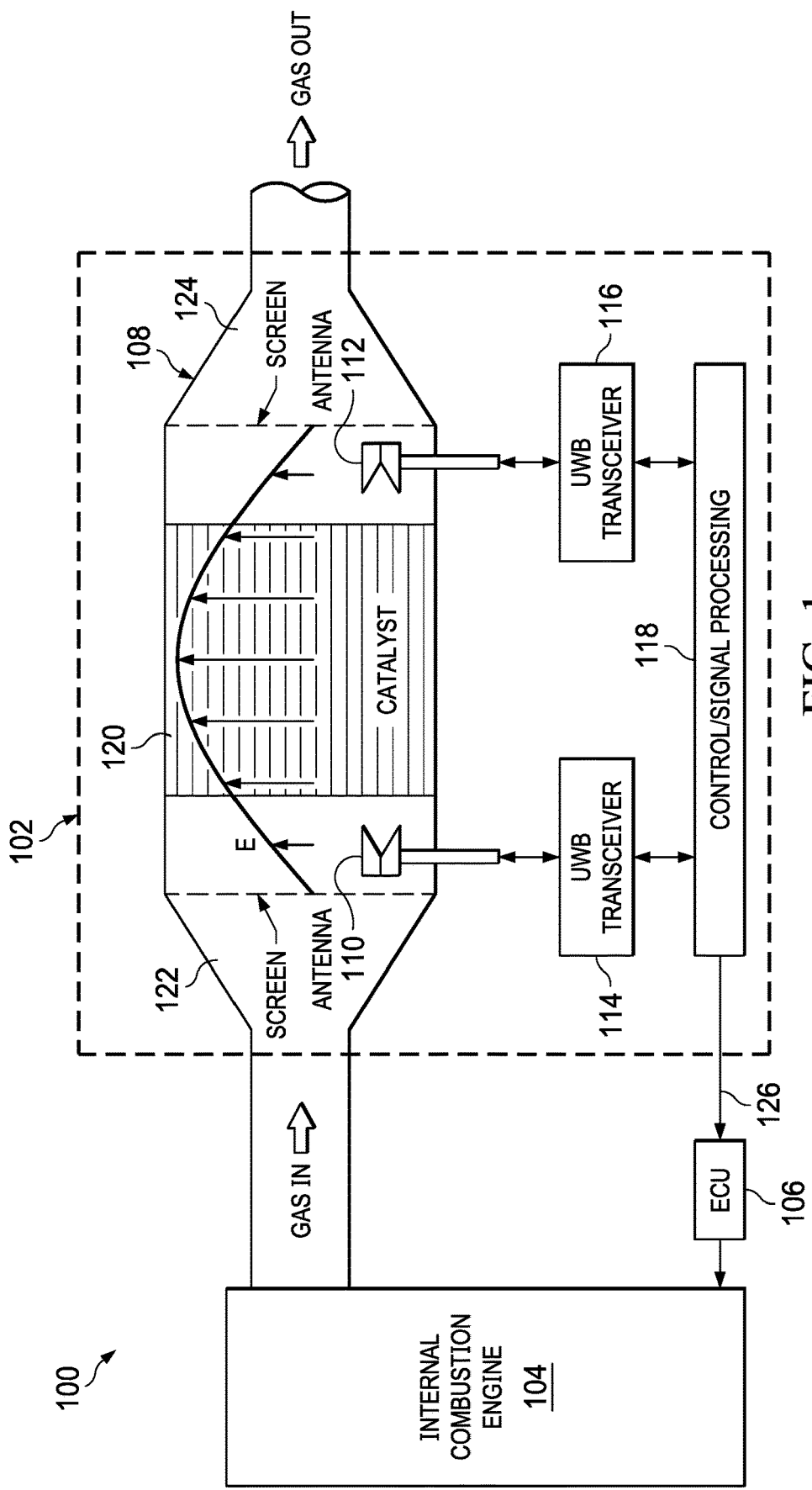
FIG. 1 shows a block diagram for an example of an exhaust gas sensing system in accordance with the present disclosure.

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

A variety of exhaust gas sensors are employed to measure the content of internal combustion engine exhaust. Oxygen sensors may be effective only when heated to relatively high temperatures, and include heating elements to raise the sensor to the necessary operating temperature. The heating element consumes power and adds complexity to the sensor. Oxygen sensors are subject to failure due contamination by combustion by-products present in the exhaust gas.

Like oxygen sensors, resistive soot sensors are disposed in the exhaust stream. Resistive soot sensors and measure soot by a change in resistance caused by soot accumulation. Such soot sensors must be periodically regenerated by heating to remove accumulated soot deposits. Regeneration consumes power, and is required to maintain operation of the resistive soot sensor.

Radio frequency soot sensors measure the absorption of radio frequency energy by soot in the exhaust. The soot changes the transmitted radio frequency power. Some such soot sensors use rod antennas for transmitting and receiving radio frequency signals. The rod antennas are fixed in length and tuned to a fixed wavelength or frequency. Consequently, the antennas operate in a narrow band covering a small band of frequencies that is sufficient only for soot sensing. The rod antennas are subject to vibration that causes inaccuracy in measurement results. Further, the rod antennas are omni-directional and, as a result, radio frequency energy is not focused on the substance to be measured. Some sensing systems that employ omni-directional antennas include a conductive screen to confine the radio frequency energy within a prescribed area.

The exhaust gas sensing system disclosed herein uses directional antennas to transmit and receive radio frequency signals. Because transmission and reception is directional, implementations may apply lower power than sensors using omni-directional antennas, and may forego use of conductive screens to confine the radio frequency signals. The directional antennas and associated electronics of the present disclosure operate over a relatively wide range of frequencies, which allows the sensing system to detect multiple substances in an exhaust stream. For example, some implementations may measure soot, oxygen and/or other substances in an exhaust stream.

FIG. 1 shows a block diagram for an example of an exhaust gas sensing system in accordance with the present disclosure. The exhaust gas sensing system 102 is a component of a combustion system 100. In FIG. 1, the combustion system 100 includes an internal combustion engine 104 and an electronic control unit 106, each of which is coupled to the exhaust gas sensing system 102. The exhaust gas sensing system 102 receives exhaust gas produced by combustion of fuel in the internal combustion engine 104 and provides exhaust gas measurements 126 to the electronic control unit 106. The electronic control unit 106 applies the exhaust gas measurements 126 to control the operation of the internal combustion engine 104. For example, the electronic control unit 106 may control the mix of fuel and air in the internal combustion engine 104 based on the exhaust gas measurements 126.

The exhaust gas sensing system 102 includes an exhaust filter 108, an antenna 110, an antenna 112, a transceiver 114, a transceiver 116, and control/signal processing circuitry 118. The exhaust filter 108 is coupled to the internal combustion engine 104. In various implementations, the exhaust filter 108 forms a channel for flow of exhaust gas in the exhaust gas sensing system 102 and may be a catalytic converter and/or a particulate filter. The exhaust filter 108 includes a filter and/or a catalyst material 120 (also referred to herein as a filter element 120) that filters and/or catalyzes selected substances present the exhaust produced by the internal combustion engine 104. The exhaust filter 108 includes an input port 122 that receives the exhaust produced by the internal combustion engine 104, and an output port 124 through which filtered exhaust gases exit the exhaust filter 108.

In the exhaust filter 108, a particulate filter captures microscopic solids (i.e., particulate) in the exhaust gas produced by the internal combustion engine 104. The particulate matter produced by some internal combustion engines 104 includes carbon particles referred to as soot. The particulate filter extracts the soot from the exhaust stream, and must undergo a regeneration process from time to time to remove the soot deposits built up in the filter. A catalytic converter converts one or more substances present in the exhaust stream to another, more desirable, substance. For example a catalytic converter may include a catalyst, such as palladium, platinum, rhodium, or other catalyst material. The catalyst material may, for example, oxidize unburned hydrocarbons present in the exhaust produced by the internal combustion engine 104 to produce carbon dioxide and water.

The exhaust gas sensing system 102 measures the content of various substances in the exhaust gas produced by the internal combustion engine 104 using radio frequency signals. The radio frequency signals propagate through the exhaust gas between the antennas 110 and 112. The antennas 110 and 112 may be ultra-wide band directional antennas that focus the radio frequency signal into a relatively tight beam between the antenna 110 and the antenna 112. In contrast, some radio frequency exhaust sensors use omni-directional antennas that require the use of a screen to restrict the radio frequency signal to a prescribed area of the exhaust filter. For example, such a screen must be embedded in the filter and/or catalyst material 120. Because the antennas 110 and 112 are directional, the exhaust gas sensing system 102 includes no such screen, which simplifies manufacturing of the exhaust filter 108. In some implementations, the antenna 110 and the antenna 112 are coplanar antennas.

Figure 4:
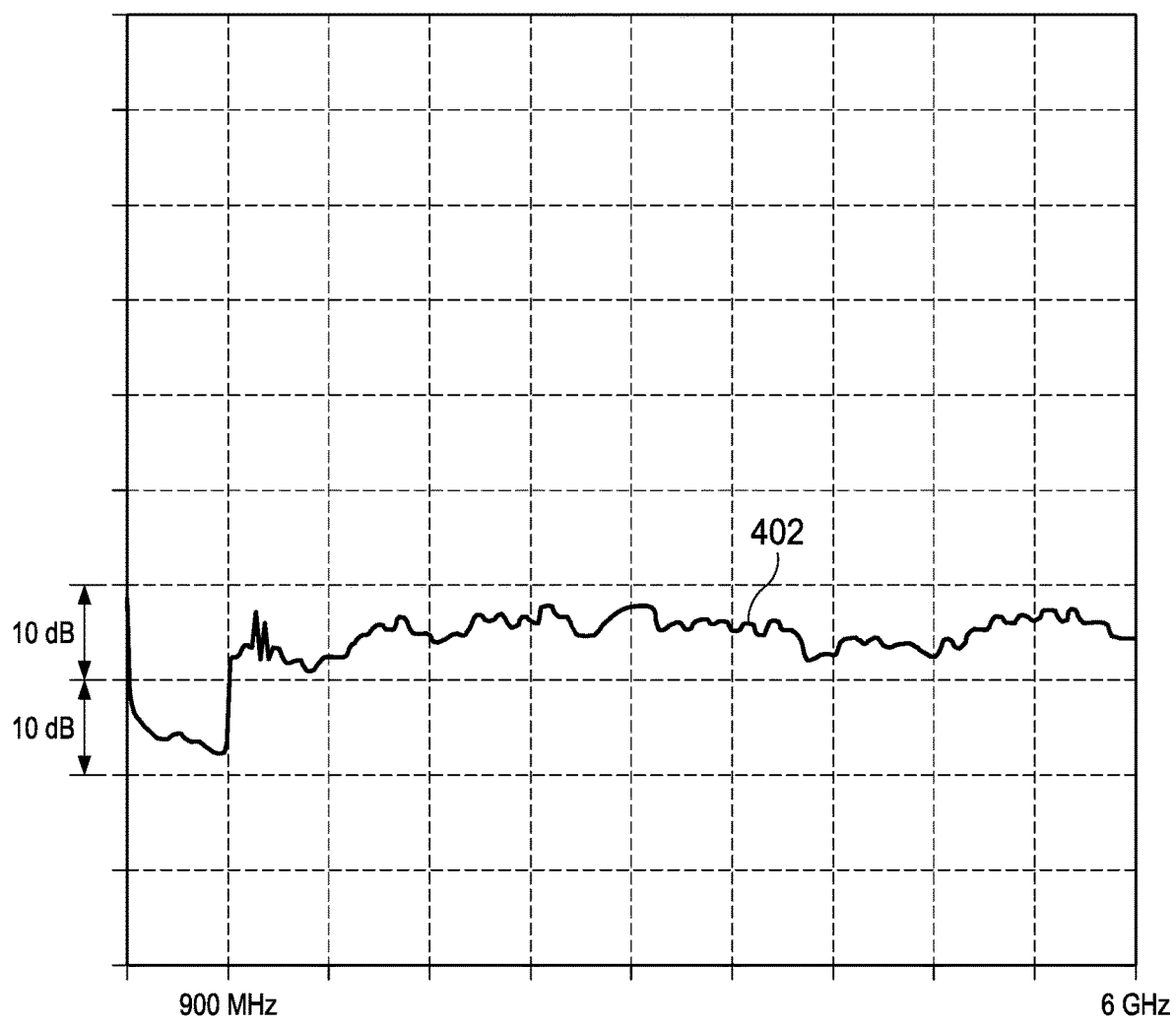
FIG. 4 shows an example of frequency response of an ultra-wide band directional antenna suitable for use in an exhaust gas sensing system in accordance with the present disclosure.

The antennas 110 and 112 are disposed in the exhaust filter 108. The antenna 110 is disposed on the one side of the filter and/or catalyst material 120 (e.g., the side of the filter and/or catalyst material 120 proximate the input port 122), and the antenna 112 is disposed on the opposite side of the filter and/or catalyst material 120 (e.g., the side of the filter and/or catalyst material 120 proximate the output port 124. Radio frequency signals propagate through the filter and/or catalyst material 120 and exhaust gas between the antennas 110 and 112. The antennas 110 and 112 can transmit and receive a wide frequency range of radio frequency signals with relatively constant power. Consequently, the exhaust gas sensing system 102 need not provide compensation for the substantial power variance in the radio frequency signals that occurs in some radio frequency exhaust sensors. For example, some implementations of a radio frequency exhaust sensor may exhibit 25 decibels of more of variance in received radio frequency (RF) signal power over a frequency range of a few gigahertz. In contrast, implementations of the antennas 110 and 112 provide a relatively constant power (e.g., less power variance than a rod antenna) from less than one gigahertz to at least six gigahertz or to at least 66 gigahertz in some implementations. FIG. 4 shows an example of frequency response of the antennas 110 and 112. Graphed power 402 shows that, in implementations of the exhaust gas sensing system 102 using the antennas 110 and 112, received radio frequency signal power variations are small relative to the power variations produced using rod or omnidirectional antennas. While the measurements of FIG. 4 illustrate a frequency range of about 900 megahertz to at least 6 gigahertz, some implementations exhibit similar performance over a frequency range of 600 megahertz to at least 66 gigahertz. Depending on the measurement setup, some embodiments may exhibit a different power variance.

Operation over a wide range of frequencies allows the exhaust gas sensing system 102 to measure multiple substances in the exhaust stream passing through the exhaust filter 108. For example, the exhaust gas sensing system 102 may measure soot in the exhaust stream and filter and/or catalyst material 120 using radio frequency signals in the gigahertz range (e.g., 2.205 gigahertz range). Oxygen has resonance at about 60 gigahertz, and can be detected using resonance harmonics. For example, oxygen content of the exhaust stream can be measured at about 30 gigahertz (using a second harmonic), 15 gigahertz (using a fourth harmonic), 12 gigahertz (using a fifth harmonic), 7.5 gigahertz (using an eighth harmonic), or 6 gigahertz (using a tenth harmonic). Some implementations of the exhaust gas sensing system 102 apply radio frequency signals at or about 6 gigahertz to measure oxygen content of the exhaust stream passing through the exhaust filter 108.

Figure 2:
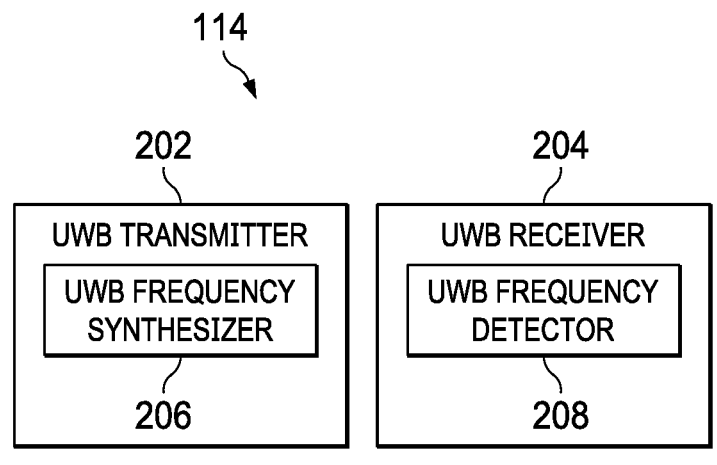
FIG. 2 shows a block diagram for an example of an ultra-wide band transceiver suitable for use in an exhaust gas sensing system in accordance with the present disclosure.

The transceiver 114 and the transceiver 116 generate and detect the multiple signal frequencies applied by the exhaust gas sensing system 102 to detect multiple substances in the exhaust stream passing through the exhaust filter 108. The antenna 110 is coupled the transceiver 114, and the antenna 112 is coupled to the transceiver 116. The transceiver 114 generates radio frequency signals for transmission via the antenna 110, and receives radio frequency signals detected by the antenna 110. Similarly, the transceiver 116 generates radio frequency signals for transmission via the 112, and receives radio frequency signals detected by the antenna 112. FIG. 2 shows a block diagram for an example of the transceiver 114, and is also applicable to the transceiver 116. The transceiver 114 includes an ultra-wide band transmitter 202 and an ultra-wide band receiver 204. The ultra-wide band transmitter 202 generates the radio frequency signals that are transmitted via the antenna 110. The ultra-wide band receiver 204 receives from the antenna 110, radio frequency signals detected by the antenna 110 (e.g., radio frequency signals transmitted via the 112). For example, to detect soot in the exhaust stream and in the filter and/or catalyst material 120 between the antennas 110 and 112, the transceiver 114 or the transceiver 116 may generate and drive the associated antenna 110 or 112 with a signal in the 0.8-0.9 gigahertz range. The transmitted radio frequency signal passes through the exhaust stream and the filter and/or catalyst material 120 between the antennas 110 and 112, is received by one of the antennas 110 and 112, converted to an electrical signal, and provided to the transceiver 114 or the transceiver 116 coupled to the receiving antenna 110 or 112. The one of the transceiver 114 or the transceiver 116 receiving the signal isolates the frequency or range of frequencies used to detect soot and determines the amplitude and/or phase of the received signal at the selected frequencies. The amplitude and/or phase of the signal at the selected frequencies is indicative of the amount of soot in the exhaust stream and the filter and/or catalyst material 120 between the antennas 110 and 112.

Similarly, to detect oxygen in the exhaust stream between the antennas 110 and 112, the transceiver 114 or the transceiver 116 may generate and drive the associated antenna 110 or 112 with a signal of about 6 gigahertz. The transmitted radio frequency signal passes through the exhaust stream between the antennas 110 and 112, is received by one of the antennas 110 and 112, converted to a electrical signal, and provided to the transceiver 114 or the transceiver 116 coupled to the receiving antenna 110 or 112. The one of the transceiver 114 or the transceiver 116 receiving the signal isolates the frequency or range of frequencies used to detect oxygen and determines the amplitude and/or phase of the received signal at the selected frequencies. The amplitude and/or phase of the signal at the selected frequencies is indicative of the amount of oxygen in the exhaust stream between the antennas 110 and 112.

The ultra-wide band transmitter 202 includes an ultra-wide band frequency synthesizer circuit 206 to generate the radio frequency signals transmitted. The ultra-wide band frequency synthesizer circuit 206 may include a phase-locked loop or other variable frequency generation circuit to produce the radio frequency signals. The ultra-wide band transmitter 202 may also include various components and circuits that have been omitted from FIG. 2 in the interest of clarity. For example, the transceiver 114 may include a power amplifier to drive the antenna 110 with the radio frequency signals generated by the ultra-wide band frequency synthesizer circuit 206.

The ultra-wide band receiver 204 includes an ultra-wide band frequency detector circuit 208 to isolate frequencies of the received radio frequency signals for measurement. For example, an implementation of the ultra-wide band frequency detector circuit 208 may include a mixer that multiplies received radio frequency signal and the output of the ultra-wide band frequency synthesizer circuit 206, and a low-pass filter that generates a DC signal from the output of the mixer, where the DC signal is representative of the amplitude of the radio frequency signal received from the antenna 110 at the frequency generated by the ultra-wide band frequency synthesizer circuit 206 (e.g., the ~6 gigahertz frequency used to measure oxygen content of the exhaust stream).

The transceiver 114 and the transceiver 116 are coupled to the control/signal processing circuitry 118. The control/signal processing circuitry 118 controls the operation of the transceiver 114 and the transceiver 116, processes the detection results produced by the transceiver 114 and the transceiver 116, and communicates measurements of substances in the exhaust stream processed by the exhaust gas sensing system 102 to the electronic control unit 106 or other systems external to the exhaust gas sensing system 102. For example, the control/signal processing circuitry 118 may select one of the transceiver 114 and the transceiver 116 to transmit a radio frequency signal, and the other of the transceiver 114 and the transceiver 116 to receive the transmitted radio frequency signal. The control/signal processing circuitry 118 may set the frequency of the radio signal transmitted and detected by communicating a frequency selection value to the transceiver 114 and the transceiver 116. The control/signal processing circuitry 118 may digitize a detection result produced by the transceiver 114 and the transceiver 116 for communication to the electronic control unit 106.

Figure 3:
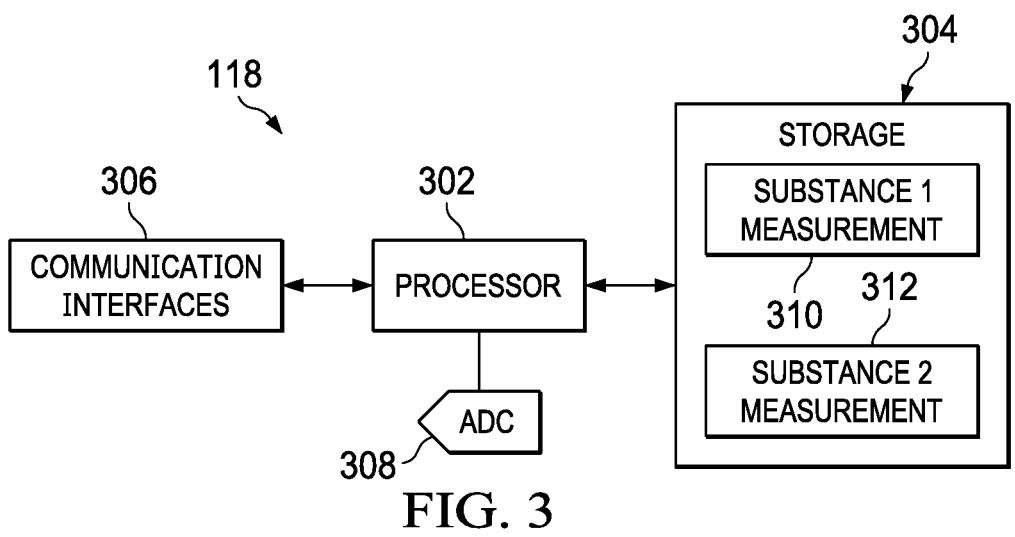
FIG. 3 shows a block diagram for an example of control/signal processing circuitry suitable for use in an exhaust gas sensing system in accordance with the present disclosure.

FIG. 3 shows a block diagram for an example of the control/signal processing circuitry 118 in accordance with the present disclosure. The control/signal processing circuitry 118 includes a processor 302, storage 304, communication interface circuitry 306, and an analog-to-digital converter 308. In some implementations the control/signal processing circuitry 118 may be a microcontroller that includes the components illustrated in FIG. 3.

The processor 302 is a circuit that executes instructions retrieved from the storage 304 to provide various programmed functions. The processor 302 may include an execution pipeline including a fetch unit, a decode unit, and an execution unit. Some examples of the processor 302 may include additional functional units, such as data and/or instruction caches, branch prediction circuitry, etc. The fetch unit retrieves instructions from storage 304 for execution.

The fetch unit provides the retrieved instructions to the decode unit. The decode unit examines the instructions received from the fetch unit, and translates each instruction into controls suitable for operating the execution unit, processor registers, and other components of the processor to perform operations that effectuate the instructions. The decode unit provides control signals to the execution unit that cause the execution unit to carry out the operations needed to execute each instruction. The execution unit may include arithmetic circuitry, shifters, multipliers, registers, logical operation circuitry, etc. that are arranged to manipulate data values as specified by the control signals generated by the decode unit. Some implementations of the processor 302 may include multiple execution units that include the same or different data manipulation capabilities.

The communication interface circuitry 306 is coupled to the processor 302. The communication interface circuitry 306 includes circuitry for communicating with circuits and systems external to the control/signal processing circuitry 118. For example the communication interface circuitry 306 may include serial communication circuitry that allows the control/signal processing circuitry 118 to communicate with the electronic control unit 106. Similarly the communication interface circuitry 306 may include serial or parallel communication circuitry that allows the control/signal processing circuitry 118 to control and or receive status and other information from the transceiver 114 and the transceiver 116. The communication interface circuitry 306 may also include analog input/output circuitry that allows the control/signal processing circuitry 118 to receive analog signals generated by the transceiver 114 and the transceiver 116.

The analog-to-digital converter 308 includes circuitry that digitizes an analog signal received by the control/signal processing circuitry 118. For example the analog-to-digital converter 308 may include a successive approximation analog-to-digital converter and associated circuitry, such as voltage reference circuitry.

The storage 304 is a non-transitory computer-readable storage medium suitable for storing instructions that are retrieved and executed by the processor 302 to perform programmed functions. The storage 304 may include volatile storage such as random access memory, non-volatile storage (e.g., FLASH storage, read-only-memory, EEPROM), or combinations thereof. The storage 304 includes instructions that are executed by the processor 302 to measure a plurality of substances in the exhaust stream passing through the exhaust gas sensing system 102. For example, in the implementation of FIG. 3, the storage 304 includes substance 1 measurement 310 and substance 2 measurement 312. Some implementations of the control/signal processing circuitry 118 may include instructions for measurement of more and/or different substances in the exhaust stream passing through the exhaust gas sensing system 102.

The substance 1 measurement 310 includes instructions that are executed by the processor 302 to measure a first substance (e.g., soot) in the exhaust stream passing through the exhaust gas sensing system 102. For example, when executed by the processor 302, the instructions of the substance 1 measurement 310 may cause the processor 302 to communicate a value of frequency to be generated to the transceiver 114 and the transceiver 116. The frequency may be selected for detection of soot (e.g., 0.8-0.9 gigahertz) or another substance present in the exhaust stream passing through the exhaust gas sensing system 102. Thereafter, the instructions may cause the processor 302 to digitize a detection signal produced by the transceiver 114 or the transceiver 116 and to communicate the digitized detection signal to the electronic control unit 106 for use in controlling the operation of the internal combustion engine 104.

Similarly, when executed by the processor 302, the instructions of the substance 2 measurement 312 may cause the processor 302 to communicate a value of frequency to be generated to the transceiver 114 and the transceiver 116. The frequency may be selected for detection of oxygen (e.g., ~6 gigahertz) or another substance present in the exhaust stream passing through the exhaust gas sensing system 102. Thereafter, the instructions may cause the processor 302 to digitize a detection signal produced by the transceiver 114 or the transceiver 116 and to communicate the digitized detection signal to the electronic control unit 106 for use in controlling the operation of the internal combustion engine 104.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A gas sensing system, comprising: a channel for flow of gas; a first directional antenna disposed in the channel; a second directional antenna disposed in the channel; a first transmitter coupled to the first directional antenna; a first receiver coupled to the second directional antenna; and signal processing circuitry coupled to the first transmitter and the first receiver, the signal processing circuity to receive first and second electrical signals from the first receiver and configured to: measure oxygen content in the channel based on a first amplitude of the first electrical signal, wherein the first electrical signal is in response to a generated first radio frequency signal at a first frequency from a plurality of radio frequency signals used to detect oxygen; and measure soot quantity in the channel based on a second amplitude of the second electrical signal, wherein the second electrical signal is in response to a generated second radio frequency signal at a second frequency from the plurality of radio frequency signals used to detect soot.

2. The gas sensing system of claim 1, further including a filter disposed in the channel between the first directional antenna and the second directional antenna.

3. The gas sensing system of claim 1, wherein the channel lacks a screen configured to constrain direction of a radio frequency signal between the first directional antenna and the second directional antenna.

4. The gas sensing system of claim 1, wherein the soot quantity of the channel corresponds to a quantity of soot in exhaust gas flowing in the channel.

5. The gas sensing system of claim 1, wherein the signal processing circuitry is configured to measure oxygen content based on a harmonic resonance frequency of the oxygen.

6. The gas sensing system of claim 1, further including:
 a second transmitter coupled to the second directional antenna;
 a second receiver coupled to the first directional antenna; and
 wherein the signal processing circuitry is coupled to the second transmitter and the second receiver.

7. The gas sensing system of claim 6, wherein the first transmitter and the second transmitter are configured to generate the plurality radio frequency signals in a range of at least 600 megahertz to 66 gigahertz, and the first receiver and the second receiver are configured to detect radio frequency signals in a range of at least 600 megahertz to an upper frequency of 66 gigahertz or a frequency having an Nth harmonic equal to 60 gigahertz.

8. The gas sensing system of claim 1, wherein the first directional antenna is oriented to direct radio frequency energy towards the second directional antenna and the second directional antenna is oriented to direct radio frequency energy towards the first directional antenna.

9. The gas sensing system of claim 1, wherein the first directional antenna and the second directional antenna are co-planar antennas.

10. The exhaust gas sensing system of claim 1, wherein the signal processing circuitry is configured to measure the oxygen content in the channel based on a phase angle of the first electrical signal.

11. The exhaust gas sensing system of claim 1, wherein the signal processing circuitry is configured to measure the soot quantity in the channel based on a phase angle of the second electrical signal.

12. An internal combustion engine control system, comprising: an exhaust filter configured to be coupled to an internal combustion engine, the exhaust filter including: an input port; an output port; a filter disposed between the input port and the output port; a sensing system, including: a first directional antenna disposed on an input port side of the exhaust filter; a second directional antenna disposed on an output port side of the exhaust filter; and signal processing circuitry coupled to the first directional antenna and the second directional antenna, the signal processing circuitry configured to receive first and second electrical signals from the first receiver and configured to: measure oxygen content in exhaust passing through the exhaust filter based on a first amplitude of a first electrical signal, wherein the first electrical signal is in response to a generated first radio frequency signal at a first frequency from a plurality of frequency signals transmitted from the first directional antenna to the second directional antenna used to detect oxygen; and measure soot quantity in exhaust passing through the exhaust filter based on a second amplitude of a second electrical signal, wherein the second electrical signal is in response to a generated second radio frequency signal at a second frequency from the plurality of frequency signals transmitted from the first directional antenna to the second directional antenna used to detect soot.

13. The internal combustion engine control system of claim 12, further including an electronic control unit coupled to the sensing system, the electronic control unit configured to control operation of the internal combustion engine based on measurements of the oxygen and the soot in the exhaust provided by the sensing system.

14. The internal combustion engine control system of claim 12, wherein the sensing system further includes:
a first transmitter coupled to the first directional antenna;
a first receiver coupled to the second directional antenna;
a second transmitter coupled to the second directional antenna;
a second receiver coupled to the first directional antenna; and
wherein the signal processing circuitry is coupled to the first transmitter, the first receiver, the second transmitter, and the second receiver.

15. The internal combustion engine control system of claim 12, wherein the exhaust filter lacks a screen configured to constrain direction of a radio frequency signal between the first directional antenna and the second directional antenna.

16. The internal combustion engine control system of claim 12, wherein the first directional antenna is oriented to direct radio frequency energy towards the second directional antenna, and the second directional antenna is oriented to direct radio frequency energy towards the first directional antenna.

17. The internal combustion engine control system of claim 12, wherein the signal processing circuitry is configured to measure the oxygen content in exhaust passing through the exhaust filter based on a phase angle of the first electrical signal.

18. The internal combustion engine control system of claim 12, wherein the signal processing circuitry is configured to measure the soot quantity in exhaust passing through the exhaust filter based on a phase angle of the second electrical signal.

19. An gas sensing system, comprising: a channel for flow of gas; a first coplanar directional antenna disposed in the channel; a second coplanar directional antenna disposed in the channel; a first transmitter coupled to the first coplanar directional antenna; a first receiver coupled to the second coplanar directional antenna; a second transmitter coupled to the second coplanar directional antenna; a second receiver coupled to the first coplanar directional antenna; signal processing circuitry coupled to the first transmitter, the first receiver, the second transmitter, and the second receiver; wherein the signal processing circuitry is configured to receive first and second electrical signals from the first receiver and is configured to: measure a quantity of soot in exhaust gas flowing in the channel based on a first amplitude of a first electrical signal, wherein the first electrical signal is in response to a generated first radio frequency signal at a first frequency from a plurality of radio frequency signals used to detect soot; and measure a quantity of oxygen in exhaust gas flowing in the channel based on a second amplitude of a second electrical signal, wherein the second electrical signal is in response to a generated second radio frequency signal at a second frequency from the plurality of radio frequency signals used to detect oxygen.

20. The exhaust gas sensing system of claim 19, wherein:
the first transmitter and the second transmitter are configured to generate radio frequency signals in a range of at least 600 megahertz to 66 gigahertz; and
the first receiver and the second receiver are configured to detect radio frequency signals in in a range of at least 600 megahertz to 66 gigahertz.

* * * * *